United States Patent [19]  [11] 4,053,536
Hughes  [45] Oct. 11, 1977

[54] DEHYDRATION OF OLEFINICALLY UNSATURATED ALCOHOLS

[75] Inventor: William B. Hughes, Bartlesville, Okla.

[73] Assignee: Phillips Petroleum Company, Bartlesville, Okla.

[21] Appl. No.: 689,759

[22] Filed: May 25, 1976

[51] Int. Cl.$^2$ .............................................. C07C 1/20
[52] U.S. Cl. .................................................. 260/681
[58] Field of Search ........................................ 260/681

[56] References Cited

U.S. PATENT DOCUMENTS

| | | | |
|---|---|---|---|
| 3,056,845 | 10/1962 | Bennett et al. | 260/681 |
| 3,351,635 | 11/1967 | Kollar | 260/681 |
| 3,960,972 | 6/1976 | Stapp | 260/681 |

Primary Examiner—C. Davis

[57] ABSTRACT

At least one unsaturated alcohol is contacted with at least one molybdenum-containing compound under reaction conditions suitable to convert at least a portion of the at least one unsaturated alcohol to at least one conjugated diene, the at least one unsaturated alcohol being selected from the group consisting of α-olefinic alcohols and β-olefinic alcohols, the at least one molybdenum-containing compound being selected from the group consisting of molybdenum β-diketonates and molybdenum (II) carboxylates.

20 Claims, No Drawings

DEHYDRATION OF OLEFINICALLY UNSATURATED ALCOHOLS

This invention relates to a process for the dehydration of α-olefinic alcohols and/or β-olefinic alcohols to conjugated dienes. In a specific aspect the invention relates to the dehydration of 3-methyl-3-buten-1-ol to isoprene.

Conjugated dienes are desirable monomeric materials which can be polymerized to provide a broad range of useful elastomers. These elastomers can, in turn, be converted to a large variety of useful rubber goods. In view of the substantial interest in conjugated dienes, significant efforts have been made to provide new and improved methods for producing the conjugated dienes.

The present invention provides a new, alternative process for the production of conjugated dienes and is particularly suitable for the conversion of 3-methyl-3-buten-1-ol to isoprene. In accordance with the present invention, at least one unsaturated alcohol is contacted with at least one molybdenum-containing compound under reaction conditions suitable to convert at least a portion of the at least one unsaturated alcohol to at least one conjugated diene, the at least one unsaturated alcohol being selected from the group consisting of α-olefinic alcohols and β-olefinic alcohols, the at least one molybdenum-containing compound being selected from the group consisting of molybdenum β-diketonates and molybdenum(II) carboxylates.

Accordingly it is an object of the present invention to provide a new process for the dehydration of α-olefinic alcohols and/or β-olefinic alcohols to conjugated dienes. Another object of the invention is to convert 3-methyl-3-buten-1-ol to isoprene. Other objects, aspects and advantages of the invention will be apparent from a study of the specification and the appended claims to the invention.

Unsaturated alcohols selected from the group consisting of α-olefinic alcohols and β-olefinic alcohols which can be employed in the process of this invention can be represented by the formula

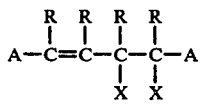

wherein each R and each A is individually selected from the group consisting of hydrogen and hydrocarbyl radicals, the number of carbon atoms in each hydrocarbyl radical being within the range of 1 to about 8, with the proviso that the two A's, together, can represent an alkylene radical having 1 to 16 carbon atoms, i.e., in a ring system; one X being hydrogen and the other X being hydroxy; the total number of carbon atoms in the alcohol molecule being in the range of 4 to about 20. Each hydrocarbyl radical can be alkyl, cycloalkyl or aryl or a combination thereof such as alkaryl, aralkyl, and the like. In the presently preferred embodiment, each A and each R is individually selected from the group consisting of hydrogen and alkyl radicals containing from 1 to 8 carbon atoms.

Examples of some unsaturated alcohols which can be employed in the process of this invention include 3-buten-2-ol, 3-buten-1-ol, 3-methyl-3-buten-2-ol, 3-methyl-3-buten-1-ol, 3-penten-2-ol, 5-ethyl-6-nonen-4-ol, 2-methyl-7-butyl-4-tridecen-6-ol, 2-methyl-4-isopropyl-5-dodecen-3-ol, 11-eicosen-10-ol, 1-cyclohexyl-5-cyclopentyl-3-penten-1-ol, 1-phenyl-4-p-tolyl-3-buten-2-ol, 3-benzyl-4-methyl-5-hexen-3-ol, 2-cyclooctyl-3-phenyl-3-buten-2-ol, 3-methylene-1-undecanol, 5-methylene-6-methyl-6-tetradecanol, 2-m-tolyl-3-(3-methylcyclopentyl)-3-buten-1-ol, 2-cyclopenten-1-ol, 3-cyclohexen-1-ol, 5-ethyl-8-phenyl-2-cycloocten-1-ol, 3-cyclododecen-1-ol, 2-cycloeicosen-1-ol, and the like, and mixtures of any two or more thereof.

The reaction can be conducted in the presence of any suitable diluent, but it is presently preferred that the unsaturated alcohol constitute the predominate portion of the total feed, more preferably at least 70 weight percent of the total feed, and even more preferably at least 85 weight percent of the total feed.

Molybdenum β-diketonates which can be employed in the process of this invention can be represented by the formula

wherein each E is individually selected from the group consisting of hydrocarbyl radicals having 1 to about 8 carbon atoms; x is 1 or 2; y is zero, 1, 2 or 3; and z is 1, 2, 3 or 4; with the proviso that when x is 1, y is zero, 1, or 2; when x is 1 and y is zero, z is 3; when x is 1 and y is 1 or 2, z is 1 or 2; and when x is 2, y is 3, and z is 4. Each hydrocarbyl radical can be alkyl, cycloalkyl, or aryl or a combination thereof such as alkaryl, aralkyl, alkylcycloalkyl and the like. In the presently preferred embodiment each E is an alkyl radical.

Examples of some molybdenum β-diketonates which can be employed in the process of this invention include oxobis(2,4-pentanedionato)molybdenum(IV), dioxo(2,4-pentanedionato)molybdenum(V), dioxobis(2,4-pentanedionato)molybdenum(VI), tris(2,4-pentanedionato)molybdenum(III), μ-oxo-dioxotetrakis-(2,4-pentanedionato)dimolybdenum(V), oxo(2,4-pentanedionato)molybdenum(III), oxobis(3,5-heptanedionato)molybdenum(IV), dioxo(2,6-dimethyl-3,5-heptanedionato)molybdenum(V), dioxobis(4,6-decanedionato)molybdenum(VI), tris(9,11-nonadecanedionato)molybdenum(III), μ-oxo-dioxotetrakis(1,3-dicyclohexyl-1,3-propanedionato)dimolybdenum(V), oxo[1-(3-methylcyclopentyl)-4-cyclopentyl-1,3-butanedionato]molybdenum(III), dioxobis(1,3-diphenyl-1,3-propanedionato)molybdenum(VI), oxobis(1-p-tolyl-4-phenyl-1,3-butanedionato)molybdenum(IV), and the like, and mixtures of any two or more thereof.

Molybdenum(II) carboxylates which can be employed in the process of this invention can be represented by the formula $(QCO_2)_2Mo$, wherein each Q is individually selected from the group consisting of hydrocarbyl radicals having 1 to about 20 carbon atoms. Each hydrocarbyl radical can be alkyl, cycloalkyl, or aryl, or a combination thereof such as alkaryl, aralkyl, and the like. In the presently preferred embodiment, each Q is an alkyl radical having 1 to 20 carbon atoms and more preferably 1 to 10 carbon atoms.

Examples of some molybdenum(II) carboxylates which can be employed in the process of this invention include molybdenum(II) acetate, molybdenum(II) acetate propionate, molybdenum(II) propionate, molybdenum(II) butyrate, molybdenum(II) 2-ethylhexanoate, molybdenum(II) undecanoate, molybdenum(II) dodecanoate, molybdenum(II) hexadecanoate, molybdenum(II) heneicosanoate, molybdenum(II) cyclohexanecarboxylate, molybdenum(II) 3-methylcyclopentanecarboxylate cyclopentylacetate, molybdenum(II) benzoate, molybdenum(II) p-toluate, molybdenum(II) phenylacetate, and the like, and mixtures of any two or more thereof.

Conjugated dienes which can be produced by the process of this invention can be represented by the formula

wherein each R and each A are as defined above. Examples of some conjugated dienes which can be produced by the process of this invention include 1,3-butadiene, isoprene, piperylene, 5-ethyl-3,5-nonadiene, 2-methyl-7-butyl-4,6-tridecadiene, 2-methyl-4-isopropyl-3,5-dodecadiene, 9,11-eicosadiene, 1-cyclohexyl-5-cyclopentyl-1,3-pentadiene, 1-phenyl-4-p-tolyl-1,3-butadiene, 3-methyl-4-benzyl-1,3-hexadiene, 2-phenyl-3-cyclooctyl-1,3-butadiene, 3-methylene-1-undecene, 5-methylene-6-methyl-6-tetradecene, 2-m-tolyl-3-(3-methylcyclopentyl)-1,3-butadiene, 1,3-cyclopentadiene, 1,3-cyclohexadiene, 1-phenyl-6-ethyl-1,3-cyclooctadiene, 1,3-cyclododecadiene, 1,3-cycloeicosadiene, and the like, and mixtures of any two or more thereof. In a presently preferred embodiment the feed, excluding any diluent, will be at least predominately composed of the α-olefinic alcohols and/or the β-olefinic alcohols, and the reaction is conducted under conditions suitable for the predominate reaction product of the dehydration of such alcohols to be the corresponding conjugated dienes.

Although the mole ratio of molybdenum-containing compound to unsaturated alcohol can be any suitable value and can vary over a broad range, generally it will be within the range of about 0.001:1 to about 0.5:1, and preferably will be in the range of about 0.005:1 to about 0.1:1.

The temperature at which the reaction is conducted can be any suitable value at which the reaction occurs and can vary over a wide range, but generally will be within the range of about 120° to about 300° C, and preferably will be in the range of about 150° to about 200° C. The reaction time can be any suitable value and can vary greatly, depending in part on the reaction temperature, but generally will be within the range of about 1 minute to about 24 hours, and preferably will be in the range of about 10 minutes to about 8 hours. The pressure is not critical and can be subatmospheric, atmospheric, or superatmospheric, e.g., in the range of about 50 to about 1,500 kPa. The reaction can be conducted in either the vapor phase or the liquid phase and in either a batch process or a continuous process.

The conjugated diene product can be separated from the reaction mixture by conventional methods such as distillation, extraction, gas chromatography, and the like. If desired, unreacted unsaturated alcohol can be recycled to the process.

EXAMPLE I

In a run within the scope of this invention, a Fisher-Porter bottle equipped with an inlet valve and a pressure gauge was charged with 0.1 g (0.001 mole) of dioxobis(2,4-pentanedionato)molybdenum(VI) and 4.0 g of a composition (hereinafter referred to as Composition A) containing 89.9 weight percent (0.042 mole) 3-methyl-3-buten-1-ol and, as impurities, 2.0 weight percent 3-methyl-2-buten-1-ol, 5.0 weight percent 3-methyl-3-butenyl formate, 1.4 weight percent 4,4-dimethyl-1,3-dioxane, 0.1 weight percent isoprene, and 1.6 weight percent other impurities. The bottle was then flushed with nitrogen and capped. The contents of the bottle were heated, with stirring, from about 25° to 148° C over a period of about 1½ hours and then from 148° to 175° C over a period of about 2 hours, after which stirring was continued at 174° C to 184° C for about 2½ hours, during which time the pressure reached a maximum of 78 psia (538 kPa). Gas chromatographic analysis of the resulting mixture showed the mixture comprised 32.1 weight percent isoprene, 33.5 weight percent 3-methyl-3-buten-1-ol, and 3.5 weight percent 3-methyl-2-buten-1-ol. Thus, isoprene was produced in substantial yield.

EXAMPLE II

In a run outside the scope of this invention, a Fisher-Porter bottle equipped with an inlet valve and a pressure gauge was charged with 4.0 g of Composition A, described in Example I. No molybdenum-containing catalyst was added. The bottle was flushed with nitrogen and capped. The contents of the bottle were heated, with stirring, from about 25° to 140° C over a period of about 1½ hours and then from 140° to 165° C over a period of about 2 hours, after which stirring was continued at 162° to 177° C for about 2½ hours, during which time the pressure reached a maximum of 50 psia (345 kPa). Gas chromatographic analysis of the resulting mixture showed the mixture comprised 90.4 weight percent 3-methyl-3-buten-1-ol, 3.5 weight percent 3-methyl-2-buten-1-ol, and 0.1 weight percent isoprene. Thus, little or no isoprene was produced in the absence of a molybdenum-containing catalyst.

Reasonable variations and modifications are possible within the scope of the foregoing disclosure and the appended claims to the invention.

That which is claimed is:

1. A process which comprises contacting at least one unsaturated alcohol with at least one molybdenum-containing compound under reaction conditions suitable to convert at least a portion of said at least one unsaturated alcohol to at least one conjugated diene, said at least one unsaturated alcohol being selected from the group consisting of α-olefinic alcohols and β-olefinic alcohols, said at least one molybdenum-containing compound being selected from the group consisting of molybdenum β-diketonates and molybdenum(II) carboxylates.

2. A process in accordance with claim 1 wherein said α-olefinic alcohols and said β-olefinic alcohols have the formula

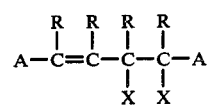

wherein each R and each A is individually selected from the group consisting of hydrogen and hydrocarbyl radicals having 1 to 8 carbon atoms, with the proviso that the two A's together can represent an alkylene radical having 1 to 16 carbon atoms; and one X is hydrogen while the other X is hydroxy; the total number of carbon atoms in the alcohol molecule being in the range of 4 to about 20.

3. A process in accordance with claim 2 wherein said molybdenum β-diketonates have the formula $$Mo_xO_y(ECCHCE)_z$$

wherein each E is individually selected from the group consisting of hydrocarbyl radicals having 1 to 8 carbon atoms; $x$ is 1 or 2; $y$ is zero, 1, 2 or 3; and $z$ is 1, 2, 3 or 4; with the proviso that when $x$ is 1, $y$ is zero, 1 or 2; when $x$ is 1 and $y$ is zero, $z$ is 3; when $x$ is 1 and $y$ is either 1 or 2, $z$ is 1 or 2; and when $x$ is 2, $y$ is 3 and $z$ is 4;

and wherein said molybdenum(II) carboxylates have the formula $$(QCO_2)_2Mo$$

wherein each Q is individually selected from the group consisting of hydrocarbyl radicals having 1 to 20 carbon atoms.

4. A process in accordance with claim 3 wherein said at least one conjugated diene has the formula $$A-C=C-C=C-A$$
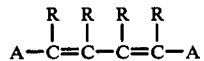

wherein each R and each A are as defined in claim 2.

5. A process in accordance with claim 4 wherein said reaction conditions comprise a temperature in the range of about 120° to about 300° C, a pressure in the range of about 50 to about 1500 kPa, and a time in the range of about 1 minute to about 24 hours.

6. A process in accordance with claim 5 wherein the mole ratio of said at least one molybdenum-containing compound to said at least one unsaturated alcohol is in the range of about 0.001:1 to about 0.5:1.

7. A process in accordance with claim 6 wherein said at least one unsaturated alcohol comprises predominately 3-methyl-3-buten-1-ol and said at least one conjugated diene comprises predominately isoprene.

8. A process in accordance with claim 7 wherein said at least one molybdenum-containing compound is at least one of said molybdenum β-diketonates.

9. A process in accordance with claim 8 wherein each E is an alkyl radical.

10. A process in accordance with claim 9 wherein said at least one molybdenum-containing compound is predominately dioxobis(2,4-pentane-dionato)molybdenum(VI).

11. A process in accordance with claim 10 wherein said reaction conditions comprise a temperature in the range of about 150° to about 200° C, and a time in the range of about 10 minutes to about 8 hours; and wherein the mole ratio of said at least one molybdenum-containing compound to said at least one unsaturated alcohol is in the range of about 0.005:1 to about 0.1:1.

12. A process in accordance with claim 1 wherein said at least one molybdenum-containing compound comprises at least one molybdenum β-diketonate having the formula $$Mo_xO_y(ECCHCE)_z$$

wherein each E is individually selected from the group consisting of hydrocarbyl radicals having 1 to 8 carbon atoms; $x$ is 1 or 2; $y$ is zero, 1, 2 or 3; and $z$ is 1, 2, 3 or 4; with the proviso that when $x$ is 1, $y$ is zero, 1 or 2; when $x$ is 1 and $y$ is zero, $z$ is 3; when $x$ is 1 and $y$ is either 1 or 2, $z$ is 1 or 2; and when $x$ is 2, $y$ is 3 and $z$ is 4.

13. A process in accordance with claim 12 wherein each E is an alkyl group.

14. A process in accordance with claim 13 wherein $x$ is 1, $y$ is 2, and $z$ is 2.

15. A process in accordance with claim 14 wherein said α-olefinic alcohols and said β-olefinic alcohols have the formula

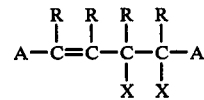

wherein each R and each A is individually selected from the group consisting of hydrogen and hydrocarbyl radicals having 1 to 8 carbon atoms, with the proviso that the two A's together can represent an alkylene radical having 1 to 16 carbon atoms; and one X is hydrogen while the other X is hydroxy; the total number of carbon atoms in the alcohol molecule being in the range of 4 to about 20.

16. A process in accordance with claim 15 wherein said at least one molybdenum-containing compound is dioxbis(2,4-pentanedionato)molybdenum(VI).

17. A process in accordance with claim 16 wherein said at least one unsaturated alcohol comprises predominately 3-methyl-3-buten-1-ol and said at least one conjugated diene comprises predominately isoprene.

18. A process in accordance with claim 1 wherein said at least one unsaturated alcohol comprises predominately 3-methyl-3-buten-1-ol and said at least one conjugated diene comprises predominately isoprene.

19. A process in accordance with claim 18 wherein said at least one molybdenum-containing compound is dioxobis(2,4-pentanedionato)molybdenum(VI).

20. A process in accordance with claim 1 wherein said at least one molybdenum-containing compound is dioxobis(2,4-pentanedionato)molybdenum(VI).

* * * * *